United States Patent [19]

Knops et al.

[11] Patent Number: 4,465,678
[45] Date of Patent: Aug. 14, 1984

[54] AMINOPROPIOPHENONE DERIVATIVES AND FUNGICIDAL USE

[75] Inventors: Hans-Joachim Knops; Wolfgang Krämer, both of Wuppertal; Paul-Ernst Frohberger, Leverkusen, all of Fed. Rep. of Germany

[73] Assignee: Bayer Aktiengesellschaft, Leverkusen, Fed. Rep. of Germany

[21] Appl. No.: 444,419

[22] Filed: Nov. 24, 1982

Related U.S. Application Data

[62] Division of Ser. No. 258,335, Apr. 28, 1981, abandoned.

[30] Foreign Application Priority Data

May 22, 1980 [DE] Fed. Rep. of Germany ....... 3019497

[51] Int. Cl.³ .................... A01N 43/34; A01N 33/24; C07C 131/00
[52] U.S. Cl. .............. 424/244; 424/248.56; 424/267; 424/274; 424/316; 424/327; 544/162; 546/232; 564/256; 564/265; 548/564; 260/239 B
[58] Field of Search ........................ 544/162; 546/232; 564/256, 245; 548/569; 260/239 B; 424/244, 248.56, 267, 274, 316, 327

[56] References Cited

U.S. PATENT DOCUMENTS 3,310,566 3/1967 Freed .................................. 546/232
3,636,111 1/1972 Karten ................................. 424/250

OTHER PUBLICATIONS

MacConaill et al., *Tetrahedron Letters*, vol. 13, (1972), pp. 1217–1220.

Primary Examiner—Robert W. Ramsuer
Attorney, Agent, or Firm—Sprung Horn Kramer & Woods

[57] ABSTRACT

Aminopropiophenone derivatives of the formula

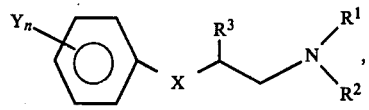

in which
X is a keto group or an oxime radical of the formula

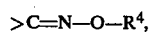

Y each independently is an alkyl radical, a halogen atom, or a halogenoalkyl, alkoxy, alkythio, halogenoalkoxy, halogenoalkylthio, cycloalkyl or cyano radical,
n is 0, 1, 2, or 3,
$R^1$ and $R^2$ each independently is an alkyl radical, or,
$R^1$ and $R^2$, together with the nitrogen atom to which they are bonded, complete an optionally substituted heterocyclic radical of the formula

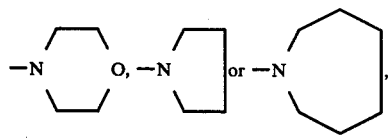

or in addition, if X is $>C=N-O-R^4$, also may complete an optionally substituted heterocyclic radical of the formula

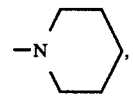

$R^3$ is a hydrogen atom or an alkyl radical, and
$R^4$ is a hydrogen atom or an alkyl, alkenyl, alkinyl or aralkyl radical,
or physiologically acceptable acid addition salts thereof, which possess fungicidal activity.

4 Claims, No Drawings

AMINOPROPIOPHENONE DERIVATIVES AND FUNGICIDAL USE

This is a division of application Ser. No. 258,335, filed Apr. 28, 1981, abandoned.

The present invention relates to certain new aminopropiophenone derivates, to several processes for their production and to their use as fungicides.

It has already been disclosed that triazolylethanol derivatives, such as 1-(4-chloro-phenyl)-2-(1,2,4-triazol-1-yl)-1-ethanol, in general have good fungicidal properties (see U.S. Ser. No. 792,756, filed May 2, 1977). However, their action is not always completely satisfactory in some fields of use, especially when low amounts and concentrations are applied.

The present invention now provides, as new compounds, the aminopropiophenone derivatives of the general formula

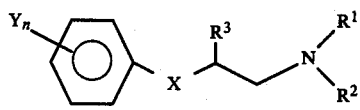

in which
R$^1$ and R$^2$ independently represent an alkyl radical; or
R$^1$ and R$^2$, together with the nitrogen atom to which they are bonded complete an optionally substituted heterocyclic radical of the formula

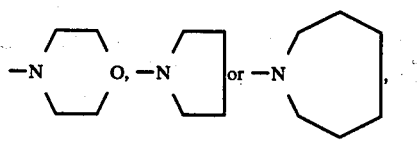

or, in addition, if X represents the oxime radical, also complete an optionally substituted heterocyclic radical of the formula

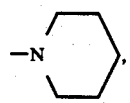

R$^3$ represents a hydrogen atom or an alkyl radical,
X represents a keto group or an oxime radical of the general formula $$>C=N-O-R^4,$$

wherein

R$^4$ represents a hydrogen atom or an alkyl, alkenyl, alkinyl or aralkyl radical, and each Y independently represents an alkyl radical, a halogen atom or a halogenoalkyl, alkoxy, alkylthio, halogenoalkoxy, halogenoalkylthio, cycloalkyl or cyano radical and n is 0, 1, 2 or 3, and physiologically acceptable acid addition salts thereof.

The compounds of the formula (I) in which X represents the oxime radical can exist in the syn-form and anti-form; they are predominantly obtained as mixtures of the two forms.

We further provide a process for the production of an aminopropiophenone derivative of the present invention, characterized in that (a) an acetophenone of the general formula

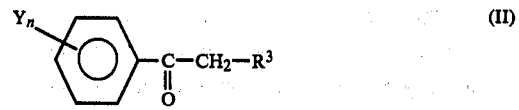

in which R$^3$, Y and n have the above-mentioned meanings, reacted with paraformaldehyde and with an amine of the general formula

in which R$^1$ and R$^2$ have the above-mentioned meanings in the presence of a diluent, to give an aminopropiophenone of the general formula

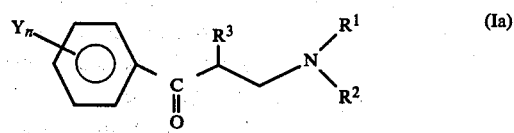

in which R$^1$, R$^2$, R$^3$, Y and n have the above-mentioned meanings, the amine of the formula (III) preferably being employed in the form of a salt thereof, and (b) if an aminopropiophenone of formula (I) in which X represents $>C=N-CR^4$ is required, the aminopropiophenone of formula (Ia) obtained as in reaction variant (a) is reacted with a salt of a hydroxylamine derivative the general formula $$H_2N-O-R^4 \quad (IV)$$

in which R$^4$ has the above-mentioned meaning,
in the presence of a diluent and in the presence of an acid-binding agent, to give an aminopropiophenone (oxime derivate) of the general formula

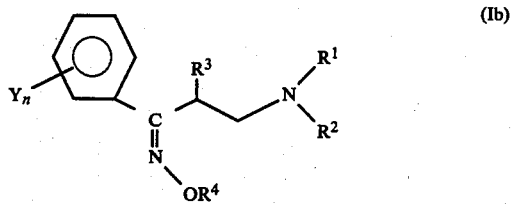

in which R$^1$, R$^2$, R$^3$, R$^4$, Y and n have the above-mentioned meanings, and (c) if an aminopropiophenone of formula (I) in which X represents $>C=N-O-R^4$ in which R$^4$ has the above-mentioned meaning, other than a hydrogen atom, is required, an alkali metal salt of an oxime derivative of formula (Ib) in which R$^4$ represents H obtained as in reaction variant (b) is reacted with a halide of the general formula $$Z-R^5 \quad (V)$$

in which

R[5] represents an alkyl, alkenyl, alkinyl or aralkyl radical and

Z represents a chlorine or bromine atom, in the presence of an organic diluent or in the presence of an organic/inorganic two-phase system in the presence of a phase transfer catalyst, the alkali metal salt of the oxime of the formula (Ib) being produced in situ, and the product of reaction variant (a), (b) or (c) is converted, if desired, into a physiologically acceptable acid addition salt thereof.

The new aminopropiophenone derivatives of the present invention have powerful fungicidal properties. Surprisingly, the compounds according to the invention exhibit a more powerful action than 1-(4-chlorophenyl)-2-(1,2,4-triazol-1-yl)-1-ethanol, which is known from the state of the art and is a compound of the same type of action. The substances according to the invention thus represent an enrichment of the art.

Preferred aminopropiophenone derivatives according to the present invention are those in which $R^1$ and $R^2$ are identical or different and represent a straight-chain or branched alkyl radical with 1 to 4 carbon atoms, or $R^1$ and $R^2$, together with the nitrogen atom to which they are bonded, complete an optionally substituted heterocyclic radical of the formula

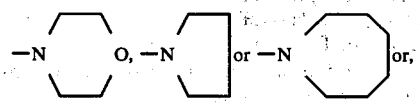

in addition, if X represents the oxime radical, complete an optionally substituted heterocyclic radical of the formula

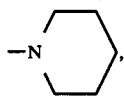

(preferred substituents being: alkyl with 1 to 4 carbon atoms or a fused-on aromatic or alicyclic ring which has 5 to 7 carbon atoms and is optionally substituted by alkyl with 1 to 4 carbon atoms or halogen), $R^3$ represents a hydrogen atom or an alkyl radical with 1 to 4 carbon atoms, X represents a keto group or an oxime radical $>C=N-O-R^4$, $R^4$ representing a hydrogen atom or a straight-chain or branched alkyl radical with 1 to 4 carbon atoms, an alkenyl or alkinyl radical with in each case 2 to 4 carbon atoms or an optionally substituted aralkyl radical with 6 to 10 carbon atoms in the aryl part and 1 or 2 carbon atoms in the alkyl part (such as, preferably, benzyl, preferred substituents being: halogen, alkyl with 1 to 4 carbon atoms, halogenoalkyl with 1 or 2 carbon atoms and 2 to 5 halogen atoms (preferably, fluorine or chlorine atoms), alkoxy or alkylthio radical with in each case 1 or 2 carbon atoms or a cyano and nitro radical, each Y independently represents a straight-chain or branched alkyl radical with 1 to 4 carbon atoms, a halogen atom, a halogenoalkyl radical with 1 or 2 carbon atoms and 2 to 5 halogen atoms (preferably, fluorine or chlorine atoms), an alkoxy or alkylthio radical with in each case 1 or 2 carbon atoms, a halogenoalkoxy or halogenoalkylthio radical with 1 to 12 carbon atoms and 2 to 5 halogen atoms (preferably, fluorine or chlorine atoms), a cycloalkyl radical with 3 to 7 carbon atoms or a cyano radical, and n is 0, 1 or 2.

Particularly preferred aminopropiophenone derivatives of the present invention are those in which $R^1$ and $R^2$ independently represent an alkyl radical with 1 to 4 carbon atoms or, together with the nitrogen atom to which they are bonded, complete an optionally substituted heterocyclic radical of the formula

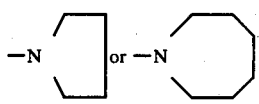

or, in addition, if X represents the oxide radical, complete an optionally substituted heterocyclic radical of the formula

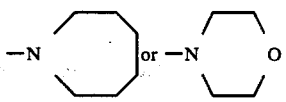

(possible substituents being methyl, ethyl and a fused-on benzene or cyclohexyl ring), $R^3$ represents a hydrogen atom or a methyl radical, X represents a keto group or an oxime radical $>C=N-O-R^4$, $R^4$ represents a hydrogen atom, a methyl, ethyl, isopropyl, n-propyl, n-butyl, tert.-butyl, vinyl, allyl or propargyl radical, or a benzyl radical which is optionally substituted by chlorine, methyl or trifluoromethyl, each Y independently represents a methyl, isopropyl or tert.-butyl radical, a fluorine or chlorine atom or a trifluoromethyl or cyclohexyl radical and n is 0, 1 or 2.

The following compounds of the general formula (I) may be mentioned specifically, in addition to the compounds mentioned in the preparative examples

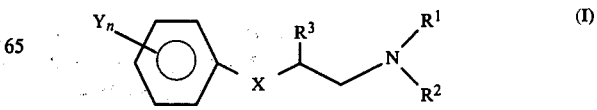

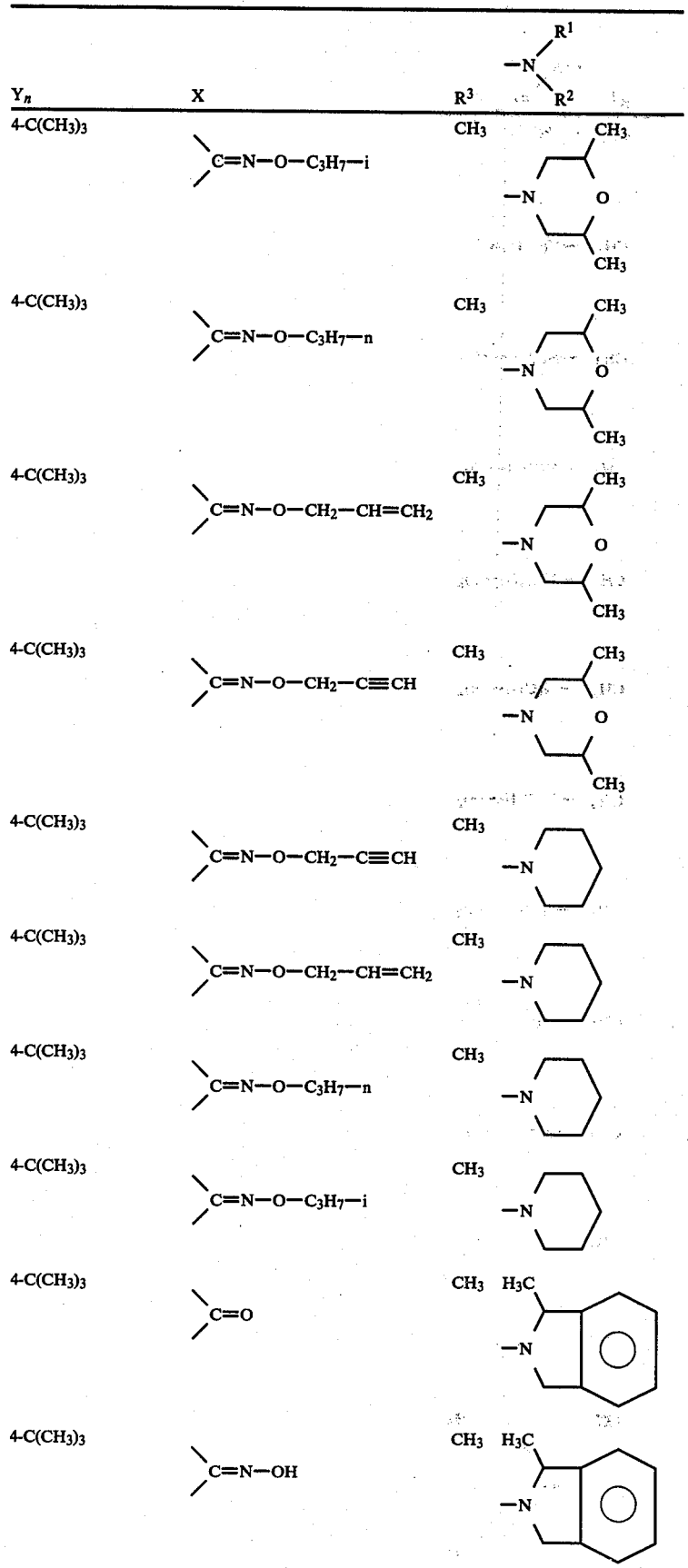

| $Y_n$ | X | $R^3$ | $-N\begin{matrix}R^1\\R^2\end{matrix}$ |
|---|---|---|---|
| 4-C(CH₃)₃ | ⟩C=N—O—C₃H₇—i | CH₃ | 2,6-dimethylmorpholino |
| 4-C(CH₃)₃ | ⟩C=N—O—C₃H₇—n | CH₃ | 2,6-dimethylmorpholino |
| 4-C(CH₃)₃ | ⟩C=N—O—CH₂—CH=CH₂ | CH₃ | 2,6-dimethylmorpholino |
| 4-C(CH₃)₃ | ⟩C=N—O—CH₂—C≡CH | CH₃ | 2,6-dimethylmorpholino |
| 4-C(CH₃)₃ | ⟩C=N—O—CH₂—C≡CH | CH₃ | piperidino |
| 4-C(CH₃)₃ | ⟩C=N—O—CH₂—CH=CH₂ | CH₃ | piperidino |
| 4-C(CH₃)₃ | ⟩C=N—O—C₃H₇—n | CH₃ | piperidino |
| 4-C(CH₃)₃ | ⟩C=N—O—C₃H₇—i | CH₃ | piperidino |
| 4-C(CH₃)₃ | ⟩C=O | CH₃ | 1-methyl-isoindoline |
| 4-C(CH₃)₃ | ⟩C=N—OH | CH₃ | 1-methyl-isoindoline |

-continued

| $Y_n$ | X | $R^3$ | $-N\begin{matrix}R^1\\R^2\end{matrix}$ |
|---|---|---|---|
| 4-C(CH₃)₃ | \C=O/ | CH₃ | $-N(C_2H_5)_2$ |
| 4-C(CH₃)₃ | \C=N—OH/ | CH₃ | $-N(C_2H_5)_2$ |
| 4-C(CH₃)₃ | \C=O/ | CH₃ | $-N(C_3H_7-i)_2$ |
| 4-C(CH₃)₃ | \C=N—OH/ | CH₃ | $-N(C_3H_7-i)_2$ |
| 4-C(CH₃)₃ | \C=O/ | CH₃ | $-N(C_3H_7-n)_2$ |
| 4-C(CH₃)₃ | \C=N—OH/ | CH₃ | $-N(C_3H_7-n)_2$ |
| 4-C(CH₃)₃ | \C=O/ | CH₃ | $-N(C_4H_9-n)_2$ |
| 4-C(CH₃)₃ | \C=N—OH/ | CH₃ | $-N(C_4H_9-n)_2$ |
| 4-C(CH₃)₃ | \C=O/ | CH₃ | $-N(C_4H_9-i)_2$ |
| 4-C(CH₃)₃ | \C=N—OH/ | CH₃ | $-N(C_4H_9-i)_2$ |
| 4-Cl | \C=O/ | CH₃ | 2,6-dimethylmorpholino |
| 4-Cl | \C=N—OH/ | CH₃ | 2,6-dimethylmorpholino |

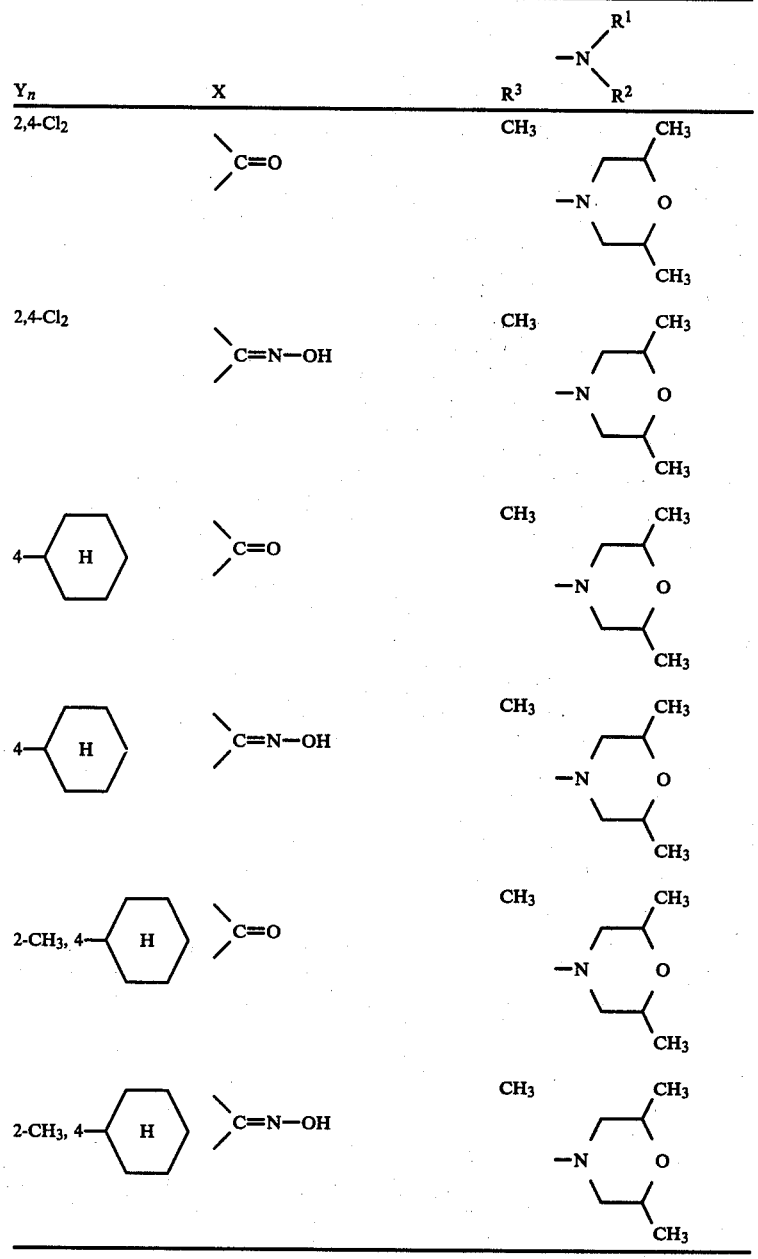

If p-tert.-butylpropiophenone, paraformaldehyde and morpholine hydrochloride are used as starting substances, the course of the reaction for the preparation of compounds of the invention is illustrated by the following equation (process variant (a)):

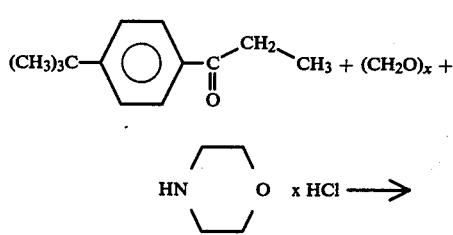

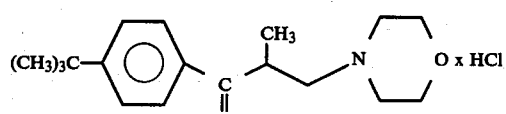

If p-tert.-butyl-2-methyl-3-morpholin-4-yl-propiophenone and hydroxylamine hydrochloride are used as starting substances, the course of the reaction for the preparation of compounds of the present invention is illustrated by the following equation (process variant (b)):

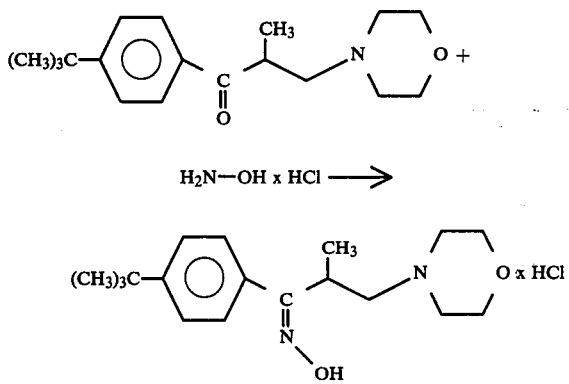

H₂N—OH x HCl ⟶

If the sodium salt of p-tert.-butyl-2-methyl-3-morpholin-4-yl-propiophenone oxime and benzyl chloride are used as starting substances, the course of the reaction for the preparation of compounds of the invention is illustrated by the following equation (process variant (c)):

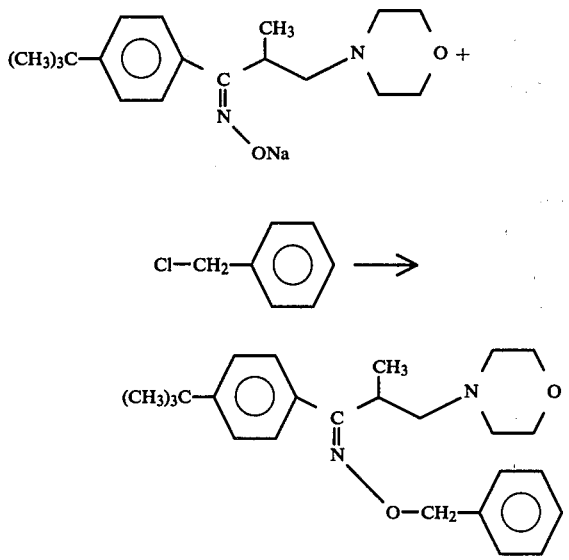

Preferred acetophenones of formula (II) to be used as starting substances for process variant (a) according to the invention are those in which $R^3$, Y and n have those meanings which have already been mentioned in connection with the description of the preferred and particularly preferred compounds according to the invention.

Preferred amines of formula (III) also to be used as starting substances for process variant (a) according to the invention are those in which $R^1$ and $R^2$ represent those radicals which have already been mentioned in connection with the description of the preferred and particularly preferred compounds according to the invention. The compounds of the formula (III) are preferably employed in the form of their hydrohalides, such as, preferably, as hydrochlorides.

The acetophenones of the formula (II) and the amines of the formula (III) are generally known compounds of organic chemistry.

The ketones of the formula (Ia) and oximes of the formula (Ib) to be used as starting substances for process variants (b) and (c) respectively are compounds according to the invention.

Preferred hydroxylamine derivatives of formula (IV) also to be used as starting substances (in the form of their salts) for process variant (b) according to the invention are those in which $R^4$ represents those radicals which have already been mentioned for this substituent in connection with the description of the preferred and particularly preferred compounds according to the invention. The compounds of the formula (IV) are preferably employed in the form of their hydrohalides, such as, preferably, the hydrochloride.

Preferred halides of formula (V) also to be used as starting substances for process variant (c) according to the invention are those in which $R^5$ represents a straight-chain or branched alkyl radical with 1 to 4 carbon atoms, an alkenyl or alkinyl radical with in each case 2 to 4 carbon atoms or an optionally substituted aralkyl radical with 6 to 10 carbon atoms in the aryl part and 1 or 2 carbon atoms in the alkyl part (such as, preferably, benzyl, preferred possible substituents being: halogen, alkyl with 1 to 4 carbon atoms, halogenoalkyl with 1 or 2 carbon atoms and 2 to 5 halogen atoms (halogen preferably being fluorine and chlorine), alkoxy and alkylthio with in each case 1 or 2 carbon atoms, cyano and nitro).

Preferred diluents for process variant (a) according to the invention are protic solvents. These include, in particular, alcohols, such as ethanol.

The reaction temperatures can be varied within a substantial range in carrying out process variant (a) according to the invention. In general, the reaction is carried out at a temperature between 20° and 150° C., preferably at a temperature between 50° and 120° C.

In carrying out process variant (a) according to the invention, 1 to 2 moles of paraformaldehyde and 1 mole of amine of the formula (III) are preferably employed per mole of acetophenone of the formula (II). The reaction is generally carried out in a weakly acid medium. Since the compounds of the formula (III) are preferably employed in the form of their salts, preferably as hydrochlorides, the end products can also be isolated directly as the salt; however, it is also possible to liberate the corresponding base in the customary manner. In each case, working up and isolation are carried out by customary methods.

Preferred diluents for process variant (b) according to the invention are protic solvents. These include, in particular, alcohols or aqueous alcohols, such as ethanol.

The reaction temperatures can be varied within a substantial range in carrying out process variant (b) according to the invention. In general, the reaction is carried out at a temperature between 20° and 120° C., preferably at a temperature between 40° and 100° C.

In carrying out the process variant (b) according to the invention, 1 to 2 moles of the compound of the formula (IV) are preferably employed per mole of ketone of the formula (Ia). Since the compounds of the formula (IV) are employed in the form of their salts, preferably as the hydrochlorides, the end products can also be isolated directly as salts; however, it is also possible to liberate the corresponding base in the customary manner. The reaction can also be carried out in the presence of an acid-binding agent, such as, preferably, alkali metal carbonates or acetates. In each case, working up and isolation are carried out by customary methods.

Possible diluents for process variant (c) according to the invention are any of the inert organic solvents. These include, preferably, ethers (such as diethyl ether and dioxane), aromatic hydrocarbons (such as toluene and benzene), and in individual cases also chlorinated hydrocarbons (such as chloroform, methylene chloride and carbon tetrachloride).

The reaction temperatures can be varied within a substantial range in carrying out process variant (c) according to the invention. In general, the reaction is carried out at a temperature between 20° and 150° C., preferably at room temperature. In individual cases it is advantageous to carry out the reaction at the boiling point of the solvent, for example, at a temperature between 60° and 100° C.

In carrying out process variant (c) according to the invention, 1 to 3 moles of halide of the formula (V) are preferably employed per mole of alkali metal salt of an oxime of the formula (Ib). Working up and isolation are carried out by customary methods.

In a preferred embodiment of process variant (c), it is expedient to follow a procedure in which an oxime of the formula (Ib) is used as the starting material, this compound is converted into the salt by means of an alkali metal hydride or amide, in a suitable inert organic solvent, and the salt is reacted immediately, without being isolated, with a halide of the formula (V), the compounds according to the invention being obtained in one operation, with elimination of an alkali metal halide.

In another preferred embodiment of process variant (c), it is expedient to carry out the preparation of the salts of the oximes of the formula (Ib) and the reaction according to the invention in a two-phase system, such as aqueous sodium hydroxide solution or potassium hydroxide solution/toluene or methylene chloride, with the addition of 0.1 to 1 mole of a phase transfer catalyst, such as an ammonium compound or phosphonium compound.

In another preferred embodiment of process variant (c), a procedure is followed in which the oxime of the formula (Ib) is reacted in the presence of alkali metal carbonates, such as, preferably, potassium carbonate, in the presence of an organic solvent, such as, preferably, dimethylformamide.

The following acids can preferably be used for the preparation of physiologically acceptable acid addition salts of the compounds of the formula (I): hydrogen halide acids (such as hydrobromic acid, and, preferably, hydrochloric acid), phosphoric acid, nitric acid, sulphuric acid, monofunctional and bifunctional carboxylic acids and hydroxycarboxylic acids (such as, acetic acid, maleic acid, succinic acid, fumaric acid, tartaric acid, citric acid, salicylic acid, sorbic acid and lactic acid) and sulphonic acids (such as p-toluenesulphonic acid and 1,5-naphthalenedisulphonic acid).

The acid addition salts of the compounds of the formula (I) can be obtained in a simple manner by customary salt formation methods, for example by dissolving a compound of the formula (I) in a suitable inert solvent and adding the acid, for example hydrogen chloride, and they can be isolated in a known manner, for example by filtration, and if appropriate purified by washing with an inert organic solvent.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compound, at the concentrations required for combating plant diseases, permits treatment of above-ground parts of plants, of vegetative propagation stock and seeds, and of the soil.

As plant protection agents, the active compounds according to the invention can be used with particularly good success for combating those fungi which cause powdery mildew diseases, thus, for combating Erysiphe species, such as against the powdery mildew of barley or of cereal causative organism (*Erysiphe graminis*); and for combating those fungi which cause scab and rust diseases, thus for combating Venturia species, such as against the apple scab causative organism (*Fusicladium dendriticum*) and Uromyces species, such as against the bean rust causative organism (*Uromyces phaseoli*).

The active compounds according to the invention also exhibit a good in vitro fungicidal action against *Fusarium nivale*.

When applied in certain amounts, the substances according to the invention also exhibit a growth-regulating action.

The active compounds can be converted into the customary formulations, such as solutions, emulsions, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsion, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

Especially in the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g are generally required.

For the treatment of soil, active compound concentrations of 0.00001 to 0.1% by weight, preferably 0.0001 to 0.02%, are required at the place of action.

The present invention also provides a fungicidal composition containing as active ingredient a compound of the present invention in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

It will be seen that the usual methods of providing a harvested crop may be improved by the present invention.

Preparative Examples

EXAMPLE 1

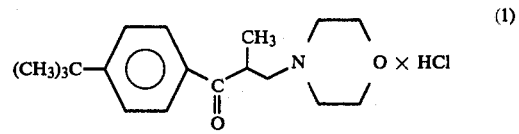

(Process variant (a))

37.07 g (0.3 mole) of morpholine hydrochloride, 57.1 g (0.3 mole) of p-tert.-butyl-propiophenone and 15.01 g (0.5 mole) of paraformaldehyde were heated under reflux in 150 ml of ethanol for 1 hour. After adding 0.5 ml of concentrated hydrochloric acid, the reaction mixture was stirred under reflux for a further 15 hours. It was then concentrated, the residue was taken up in chloroform, the chloroform mixture was washed twice with water and the organic phase was dried over sodium sulphate and concentrated. The crystalline residue was suspended in hot ethyl acetate, filtered off and dried. 60 g (61.5% of theory) of p-tert.-butyl-2-methyl-3-morpholin-4-yl-propiophenone hydrochloride of melting point 189° to 91° C. were obtained.

EXAMPLE 2

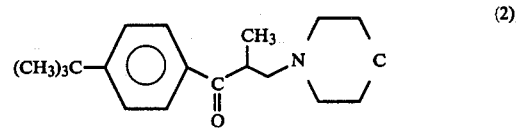

The hydrochloride obtained according to Example 1 was dissolved in aqueous sodium bicarbonate solution, the solution was then extracted with ethyl acetate and the product phase was concentrated. A quantitative yield of p-tert.-butyl-2-methyl-3-morpholin-4-yl-propiophenone of melting point 71° to 73° C. was obtained.

EXAMPLE 3

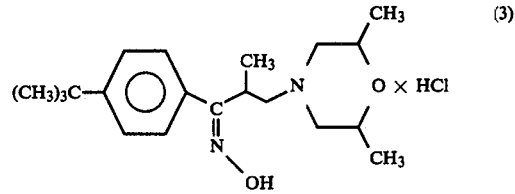

(Process variant (b))

9.5 g (0.03 mole) of p-tert.-butyl-2-methyl-3-(2,6-dimethyl-morpholin-4-yl)-propiophenone were heated under reflux with 3.6 g (0.05 mole) of hydroxylamine hydrochloride in 80 ml of ethanol for 20 hours. After cooling to 5° C., the mixture was filtered. The filtrate was concentrated, the residue was suspended in dilute sodium hydroxide solution and the suspension was extracted with chloroform. Ethereal hydrochloric acid was added to the organic phase and the reaction product which had precipitated was filtered off. 10.6 g (96% of theory) of p-tert.-butyl-2-methyl-3-(2,6-dimethyl-morpholin-4-yl)-propiophenone oxime hydrochloride of melting point 214° to 16° C. were obtained.

EXAMPLE 4

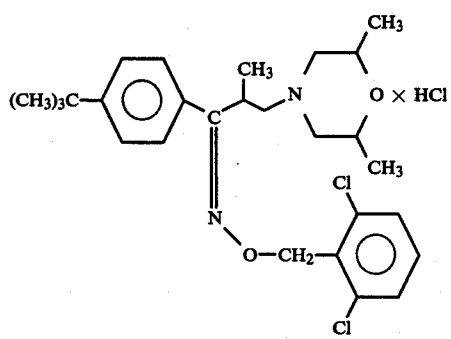

(4)

(Process variant (b))

9.5 g (0.03 mole) of p-tert.-butyl-2-methyl-3-(2,6-dimethyl-morpholin-4-yl)-propiophenone, 6.2 g (0.03 mole) of 2,6-dichlorobenzyl-hydroxylamine hydrochloride and 2.2 g of sodium acetate were stirred under reflux in 60 ml of ethanol for 55 hours. After cooling, the mixture was filtered, the filtrate was concentrated and the residue was taken up in 50 ml of methylene chloride. The methylene chloride mixture was washed with water and sodium bicarbonate solution and again with water, dried over sodium sulphate and concentrated. The oily residue was dissolved in petroleum ether and the solution was filtered. The filtrate was treated with active charcoal and concentrated again. The residue was taken up in ether, ethereal hydrochloric acid was added and the mixture was concentrated. 5 g (35% of theory) of p-tert.-butyl-2-methyl-3-(2,6-dimethylmorpholin-4-yl)-propiophenone oxime O-2,6-dichlorobenzyl ether hydrochloride of melting point 158°–67° C. were obtained.

The following compounds of the general formula

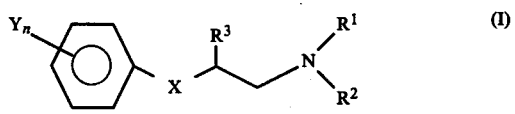

(I)

were obtained in a corresponding manner and according to the processes variants indicated above:

| Compound | $Y_n$ | X | $R^3$ | $-N\begin{smallmatrix}R^1\\R^2\end{smallmatrix}$ | Melting point (°C.) or boiling point (°C./mm Hg column) |
|---|---|---|---|---|---|
| 5 | 4-C(CH$_3$)$_3$ | \>C=O | CH$_3$ | —N(2,6-dimethylmorpholino) | 145–48/0.12 |
| 6 | 4-C(CH$_3$)$_3$ | \>C=N—OH | CH$_3$ | —N(morpholino) | 202–03 (decomposition)/(× HCl) |
| 7 | 4-C(CH$_3$)$_3$ | \>C=N—OH | CH$_3$ | —N(morpholino) | oil |
| 8 | 4-C(CH$_3$)$_3$ | \>C=N—OH | CH$_3$ | —N(piperidino) | 214–16 (decomposition)/(× HCl) |
| 9 | 4-C(CH$_3$)$_3$ | \>C=O | CH$_3$ | —N(hexamethyleneimino) | 178–80 (× HCl) |
| 10 | 4-C(CH$_3$)$_3$ | \>C=O | CH$_3$ | —N(hexamethyleneimino) | oil |

-continued

| Compound | $Y_n$ | X | $R^3$ | $-N\begin{matrix}R^1\\R^2\end{matrix}$ | Melting point (°C.) or boiling point (°C./mm Hg column) |
|---|---|---|---|---|---|
| 11 | 4-C(CH$_3$)$_3$ | \C=N—OH | CH$_3$ | -N (azocane, 7-membered) | 194–97 (× HCl) |
| 12 | — | \C=O | CH$_3$ | —N(C$_2$H$_5$)$_2$ | 120–24 (× HCl) |
| 13 | 4-C(CH$_3$)$_3$ | \C=O | CH$_3$ | —N(CH$_3$)$_2$ | 181–82 (× HCl) |
| 14 | 4-C(CH$_3$)$_3$ | \C=O | CH$_3$ | -N (pyrrolidine) | 171–72 (× HCl) |
| 15 | 4-C(CH$_3$)$_3$ | \C=N—O—CH$_2$—(2,6-diCl-phenyl) | CH$_3$ | -N (piperidine) | oil |
| 16 | 4-C(CH$_3$)$_3$ | \C=O | CH$_3$ | -N (azetidine) | 47–49 |
| 17 | 4-C(CH$_3$)$_3$ | \C=N—OH | CH$_3$ | -N (pyrrolidine) | 189–92 (× HCl) |
| 18 | 4-C(CH$_3$)$_3$ | \C=N—OH | CH$_3$ | —N(CH$_3$)$_2$ | 170–72 (× HCl) |
| 19 | 4-C(CH$_3$)$_3$ | \C=O | CH$_3$ | —N(CH$_3$)$_2$ | oil |
| 20 | 4-C(CH$_3$)$_3$ | \C=O | CH$_3$ | -N (1,2,3,4-tetrahydroquinoline) | 115–20 (× HCl) |
| 21 | 4-C(CH$_3$)$_3$ | \C=O | CH$_3$ | —N(C$_2$H$_5$)$_2$ | 134 (× HCl) |
| 22 | 4-C(CH$_3$)$_3$ | \C=O | CH$_3$ | —N(C$_2$H$_5$)$_2$ | oil |

-continued

| Compound | $Y_n$ | X | $R^3$ | $-N\begin{smallmatrix}R^1\\R^2\end{smallmatrix}$ | Melting point (°C.) or boiling point (°C./mm Hg column) |
|---|---|---|---|---|---|
| 23 | 4-C(CH$_3$)$_3$ | \C=O | CH$_3$ | —N(C$_3$H$_7$)$_2$ | 120 (× HCl) |
| 24 | 4-C(CH$_3$)$_3$ | \C=O | CH$_3$ | —N(C$_3$H$_7$)$_2$ | oil |
| 25 | 4-C(CH$_3$)$_3$ | \C=N—O—CH$_2$—O CH$_2$ | CH$_3$ | 2,6-dimethylmorpholino | 144–52 (× HCl) |
| 26 | 4-C(CH$_3$)$_3$ | \C=N—OH | CH$_3$ | —N(C$_3$H$_7$)$_2$ | 129 (× HCl) |
| 27 | 4-C(CH$_3$)$_3$ | \C=N—OH | CH$_3$ | —N(C$_2$H$_5$)$_2$ | 125 (× HCl) |
| 28 | 4-C(CH$_3$)$_3$ | \C=N—O—CH$_2$—C≡CH | CH$_3$ | 2,6-dimethylmorpholino | oil |
| 29 | 4-C(CH$_3$)$_3$ | \C=N—O—CH(CH$_3$)$_2$ | CH$_3$ | 2,6-dimethylmorpholino | oil |
| 30 | 4-C(CH$_3$)$_3$ | \C=N—O—CH$_2$—CH$_2$—CH$_3$ | CH$_3$ | 2,6-dimethylmorpholino | oil |
| 31 | 4-C(CH$_3$)$_3$ | \C=O | CH$_3$ | —N(CH(CH$_3$)$_2$)$_2$ | 152–156 (× HCl) |
| 32 | 4-C(CH$_3$)$_3$ | \C=O | CH$_3$ | —N(CH$_2$—CH(CH$_3$)$_2$)$_2$ | 278–280 (× HCl) |
| 33 | 4-C(CH$_3$)$_3$ | \C=O | CH$_3$ | —N(CH$_2$—CH$_2$—CH$_2$—CH$_3$)$_2$ | 103–106 (× HCl) |

-continued

| Compound | $Y_n$ | X | $R^3$ | $-N{<}^{R^1}_{R^2}$ | Melting point (°C.) or boiling point (°C./mm Hg column) |
|---|---|---|---|---|---|
| 34 | 4-C(CH$_3$)$_3$ | \C=N—OH/ | CH$_3$ | $-N{<}^{CH(CH_3)_2}_{CH(CH_3)_2}$ | oil |
| 35 | 4-C(CH$_3$)$_3$ | \C=N—OH/ | CH$_3$ | $-N{<}^{CH_2-CH(CH_3)_2}_{CH_2-CH(CH_3)_2}$ | oil |
| 36 | 4-C(CH$_3$)$_3$ | \C=N—OH/ | CH$_3$ | $-N{<}^{CH_2-CH_2-CH_3-CH_3}_{CH_2-CH_2-CH_2-CH_3}$ | oil |

The fungicidal activity of the compounds of this invention is illustrated by the following example wherein the compounds according to the present invention are each identified by the number (given in brackets) from the preparative examples hereinabove.

The known comparison compound is identified as follows:

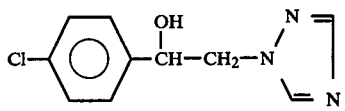 (A)

EXAMPLE 5

Erysiphe test (barley)/protective/
Solvent: 100 parts by weight of dimethylformamide
Emulsifier: 0.25 part by weight alkylaryl polyglycol ether To produce a suitable preparation of active compound, 1 part by weight of active compound was mixed with the stated amounts of solvent and emulsifier, and the concentrate was diluted with water to the desired concentration.

To test for protective activity, young plants were sprayed with the preparation of active compound until dew-moist. After the spray coating had dried on, the plants were dusted with spores of *Erysiphe graminis f.sp. hordei*.

The plants were placed in a greenhouse at a temperature of about 20° C. and a relative atmospheric humidity of about 80%, in order to promote the development of powdery mildew pustules.

Evaluation was carried out 7 days after the inoculation.

In this test, a significantly superior activity compared with comparison compound (A) was shown, for example, by the compounds (5), (3), (4), (1), (2), (6), and (8).

It will be appreciated that the instant specification and examples are set forth by way of illustration and not limitation, and that various modifications and changes may be made without departing from the spirit and scope of the present invention.

What is claimed is:

1. An aminopropiophenone derivative of the formula

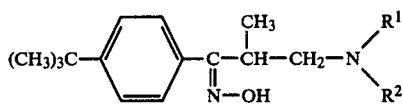

in which $R^1$ and $R^2$ each independently is an alkyl radical,
or a physiologically acceptable acid addition salt thereof.

2. A compound according to claim 1, in which $R^1$ and $R^2$ each independently is an alkyl radical with 1 to 4 carbon atoms,
or a physiologically acceptable acid addition salt of a hydrogen halide acid, phosphoric acid, nitric acid, sulphuric acid, a monofunctional or bifunctional carboxylic acid or hydroxy-carboxylic acid, or a sulphonic acid.

3. A method of combating fungi comprising applying to the fungi, or to a habitat thereof, a fungicidally effective amount of an aminopropiophenone derivative of the formula

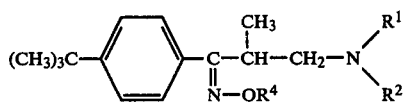

in which
$R^1$ and $R^2$ each independently is an alkyl radical, or, $R^1$ and $R^2$, together with the nitrogen atom to which they are bonded, complete an optionally substituted heterocyclic radical of the formula

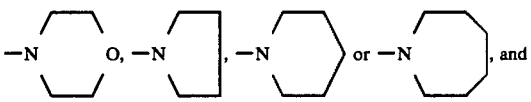

$R^4$ is a hydrogen atom or an alkyl, alkenyl, alkinyl or aralkyl radical,
or a physiologically acceptable acid addition salt thereof.

4. The method according to claim 2, wherein such compound is p-tert.-butyl-2-methyl-3-(2,6-dimethyl-morpholin-4-yl)-propiophenone oxime,
p-tert.-butyl-2-methyl-3-morpholin-4-yl-propiophenone oxime, or
p-tert.-butyl-2-methyl-3-piperidin-1-yl-propiophenone oxime,
or a physiologically acceptable acid addition salt thereof.

* * * * *